United States Patent [19]

Castro et al.

[11] Patent Number: 5,520,704
[45] Date of Patent: May 28, 1996

[54] EVERTING FORCEPS WITH LOCKING MECHANISM

[75] Inventors: Michael Castro, Seymour, Conn.; Kenneth E. Toso, Portchester, N.Y.

[73] Assignee: United States Surgical Corporation, Norwalk, Conn.

[21] Appl. No.: 958,633

[22] Filed: Oct. 9, 1992

[51] Int. Cl.$^6$ .................................................. A61B 17/42
[52] U.S. Cl. ........................... 606/208; 606/205; 606/210; 606/207
[58] Field of Search ........................... 294/99.2; 433/154, 433/159; 606/205, 206, 207, 208, 210, 211

[56] References Cited

U.S. PATENT DOCUMENTS

| | | |
|---|---|---|
| 99,050 | 1/1870 | Battle . |
| 293,718 | 2/1884 | Clark . |
| 715,612 | 12/1902 | Van Schott . |
| 781,277 | 1/1905 | Fahey . |
| 1,033,942 | 7/1912 | Ruggles . |
| 1,198,958 | 9/1916 | Risley ........................... 294/99.2 |
| 2,214,984 | 9/1940 | Bachmann ........................... 606/210 |
| 3,140,715 | 7/1964 | Whitton, Jr. et al. . |
| 3,265,068 | 8/1966 | Holohan . |
| 3,809,094 | 5/1974 | Cook ........................... 606/210 |
| 3,904,033 | 9/1975 | Haerr ........................... 604/162 |
| 4,024,870 | 5/1977 | Sandel . |
| 4,192,204 | 3/1980 | Feldman . |
| 4,192,313 | 3/1980 | Ogami . |
| 4,424,811 | 1/1984 | Groot . |
| 4,574,805 | 5/1986 | Lerner . |
| 4,593,693 | 6/1986 | Schenck . |
| 4,657,019 | 4/1987 | Walsh et al. . |
| 4,724,838 | 2/1988 | Hasson . |
| 4,727,876 | 3/1988 | Porat et al. . |
| 4,793,349 | 12/1988 | Weinrib . |
| 4,800,880 | 1/1989 | Catalano . |
| 4,950,281 | 8/1990 | Kirsch et al. ........................... 606/207 |
| 5,015,252 | 5/1991 | Jones . |
| 5,019,091 | 5/1991 | Porat et al. . |
| 5,047,046 | 9/1991 | Bodoia . |
| 5,104,397 | 4/1992 | Vasconcelos et al. . |
| 5,156,431 | 10/1992 | Lowe . |

FOREIGN PATENT DOCUMENTS 1110359 7/1961 Germany .

Primary Examiner—C. Fred Rosenbaum
Assistant Examiner—N. Kent Gring

[57] ABSTRACT

An everting forceps comprising first and second outer resilient legs rigidly interconnected at one end thereof, and a third leg intermediate the pair of legs. Each of the outer legs terminating at a tip provided with an arcuate jaw. A moving device positions the intermediate leg with respect to one of the first and second legs. A locking mechanism for locking the intermediate leg and at least one of the outer legs is also provided.

35 Claims, 3 Drawing Sheets

5,520,704

EVERTING FORCEPS WITH LOCKING MECHANISM

BACKGROUND OF THE INVENTION

This invention relates to the field of surgery and more particularly to a tool useful for performing anastomoses and having a locking mechanism.

The term "anastomosis" covers a variety of procedures in which blood vessels or other tubular members, such as parts of the colon, are joined or reconnected. Vessels may be joined in a variety of relative orientations, including end-to-end and end-to-side. Solid tubular structures such as peripheral nerves can also be joined together, as well as solid structures such as subcutaneous tissue and skin.

Anastomoses are traditionally performed by joining, clipping or suturing the vessels together at the juncture between them. Alternatives to suturing have been developed, in order to prevent thrombosis which tends to occur at the points of penetration of the sutures. One such alternative, particularly for larger vessels, involves mechanical connectors such as collars. A second alternative to suturing is the use of surgical clips which are applied along the vessel juncture to perform a holding function similar to that of sutures, without penetrating the vessel walls. Two such non-penetrating clips are shown in U.S. Pat. Nos. 4,586,503 and 4,733,660 to Kirsch et al. As described in the former patent, the non-penetrating clips are applied over apposed edges of the vessels, the edges first being everted, or turned outward, to form flanges that are gripped between the jaws of the clips. Eversion not only enables the clip jaws to better grip the vessels, but also insures that only the interior surfaces of the vessels are in contact.

The use of such non-penetrating clips requires that the vessel or tissue edges be accurately and symmetrically everted. Correct eversion is critical at the beginning of anastomoses and at difficult sites, such as at the heel and toe of an end-to-side anastomosis.

For an astomosis, a blood vessel is everted by rotating the exposed end of the vessel such that the vessel's intima is exposed and is transverse to the longitudinal axis of the vessel. During anastomosis, this part of the vessel end must be everted and held in close relationship while the final steps of joining the blood vessels are performed. The fact that surgical clips have proven fast, simple to apply and reliable in their holding ability, has accentuated the need for a tool to assist a surgeon in everting vessels while performing anastomoses.

Clips are typically applied with a small hand-held tool that enables the surgeon to precisely place the clip over the tissue edges, and then to close the dip, as by applying a squeezing pressure to the tool. It is desirable to enable the same surgeon to perform the required vessel eversion, with his free hand.

One example of a prior art everting forcep is disclosed in U.S. Pat. No. 4,950,281 to Kirsch et al., the contents of which are hereby incorporated by reference, where the forceps include a pair of outer legs and an inner leg all cooperating jaws are mounted at the ends of the respective relatively movable legs. The outer legs can be independently manipulated to evert a vessel for anastomosis procedure.

It would be desirable to provide a mechanism in the everting forceps which could lock one of the legs during manipulation of the other leg. This would advantageously allow the surgeon to release his grip on the locked legs to evert the other vessel with the unlocked leg. The forceps is used by grabbing the vessel between one outer leg and the intermediate leg and everting the vessel. The user maintains pressure on these two legs while the opposing vessel is grabbed and everted by the second free outer leg in cooperation with the intermediate leg.

SUMMARY OF THE INVENTION

In view of the foregoing, the invention comprises an everting forceps, comprising a pair of outer, resilient legs rigidly interconnected at one end thereof, a third leg intermediate the pair of legs, the outer and intermediate legs having respective tips at their free ends, the tips being provided with respective jaws, and further comprising manipulable means connected to the intermediate leg for enabling one to move the intermediate leg to be moved with respect to one of the outer legs. A locking mechanism is provided which enables at least one of the outer legs to be locked relative to the intermediate leg.

BRIEF DESCRIPTION OF THE DRAWINGS

The present invention will be more fully appreciated as the same becomes better understood from the following detailed description of the present invention when considered in connection with the following drawings in which.

DESCRIPTION OF THE PREFERRED EMBODIMENT

Figure 1:
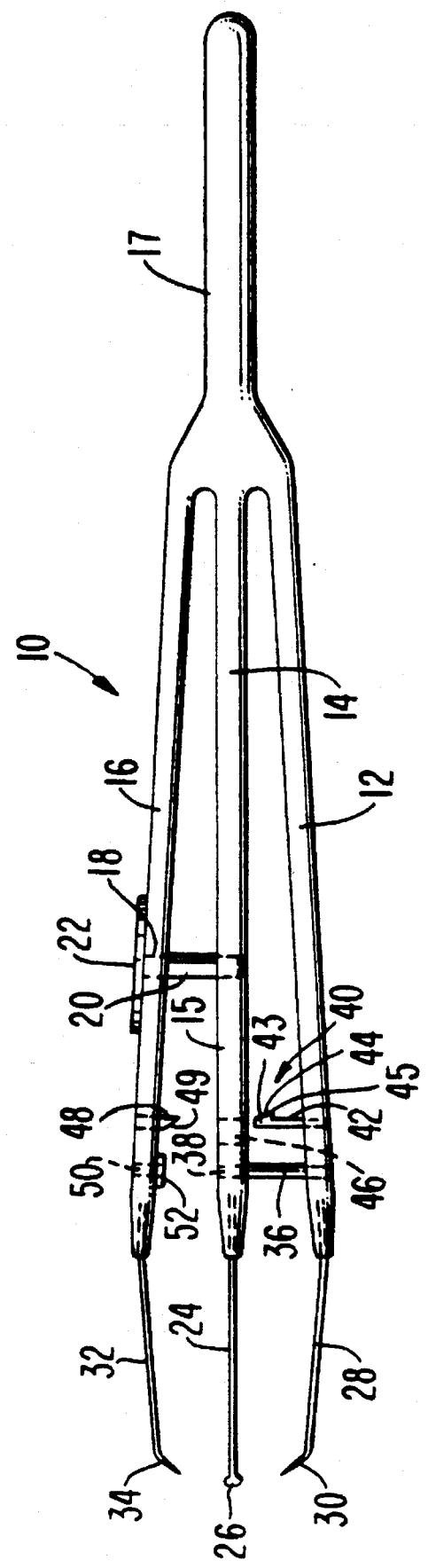
FIG. 1 is a side view of a tool of the present invention shown in an open position.

FIG. 1 shows an everting forceps 10 embodying the invention. The forceps includes three handles 12, 14, 16 of plastic resilient material or spring metal, interconnected in laminar fashion at the proximal end to form a connection head 17. For convenience, the outer handles or legs 12 and 16 are referred to as the lower and upper handles, respectively, according to their position in FIG. 1, although no particular orientation of the tool is required in use.

The intermediate handle 14 extends between the lower and upper handles 12 and 16, both of which are bowed outwardly along their unconnected portions, away from the intermediate handle 14. The intermediate handle includes a first opening 46 for engaging a locking mechanism 40 and locking the intermediate handle 14 relative to the lower handle 12. A second opening 46 is formed in the intermediate handle 14 for receiving a portion of stabilizing member 36. The distal end of the intermediate handle 14 includes a leg 24 which tapers towards a tip 26 preferably having, as is shown in the figure, a spherical tip of the type described in U.S. Pat. No. 4,950,281 incorporated herein by reference; although the shape of the tip may be modified as desired for particular applications.

The upper handle 16 has an aperture 18 near its midpoint, through which a transverse shaft 20 extends. The shaft is welded to the intermediate handle 14 and has a button end 22 affixed thereon outside of the upper handle 16. The button 22 enables the surgeon to manipulate and position the intermediate handle 14 via movement of upper handle 16, thereby engaging or disengaging the locking mechanism 40, as described hereafter. The upper handle 16 also includes an opening 50 having a guide cap 52 for receiving a portion of stabilizing member 36.

Figure 2:
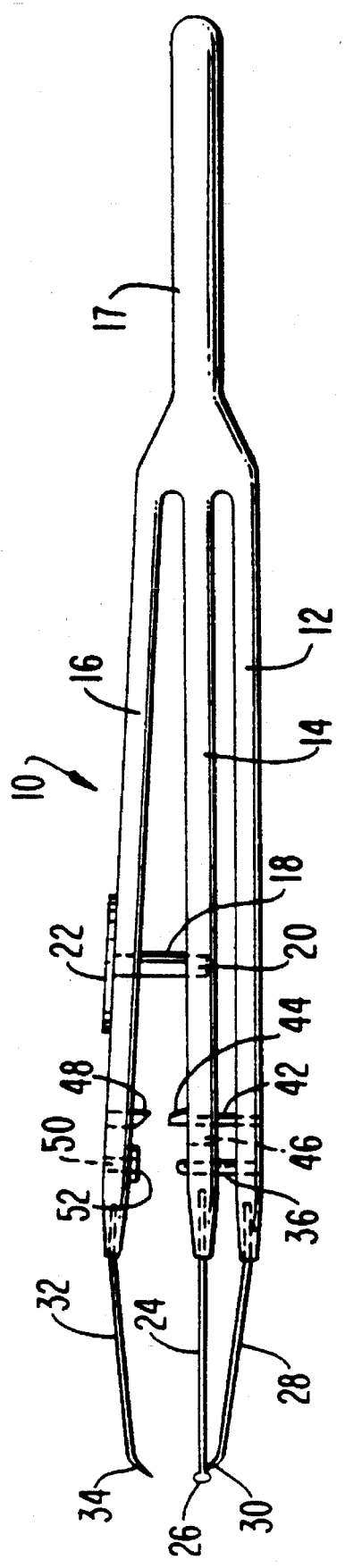
FIG. 2 is a side view of the tool of the present invention shown with one leg engaged by the locking mechanism.
Figure 3:
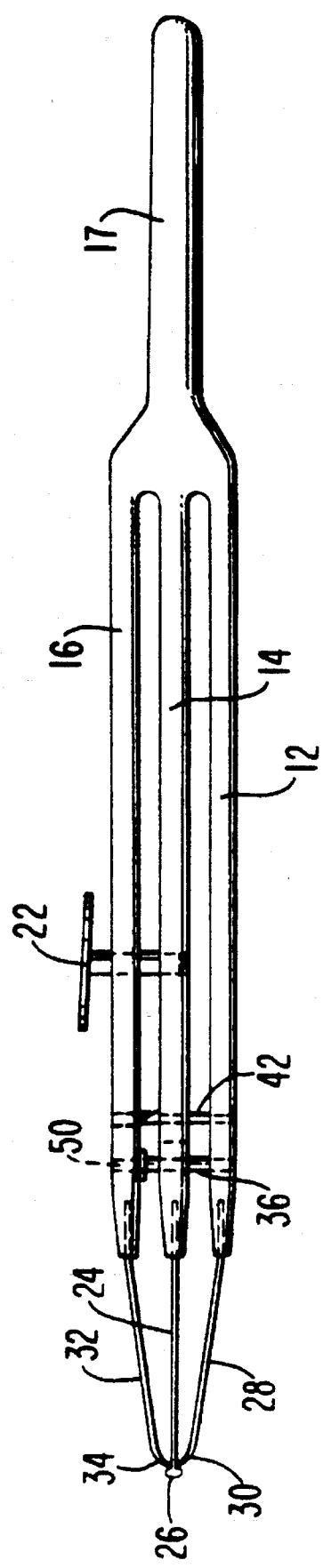
FIG. 3 is a side view of the tool of the present invention shown in a locked and fully closed position.
Figure 4:
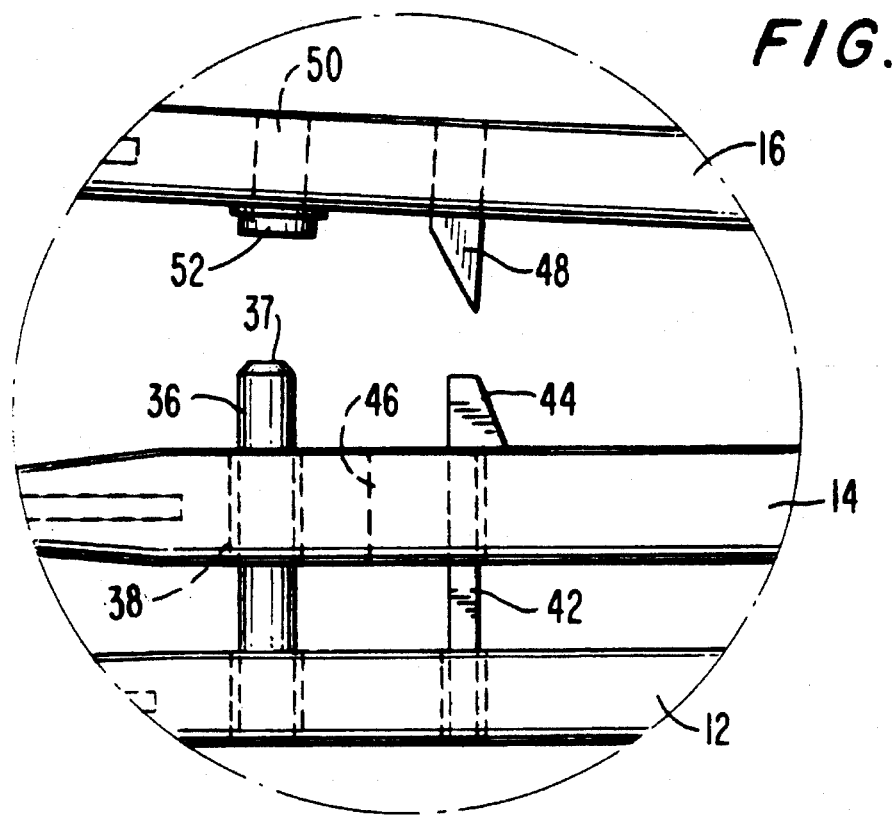
FIG. 4 shows a detailed side view of the locking mechanism of the present invention shown in a unlocked position.

The upper and lower handles 12, 16 have similarly connected legs 28, 32 which are tapered and bent inwardly near their distal ends and terminate at similar jaws 30, 34. The legs 28, 32 extend into and are fixedly attached to the respective handles 12, 16. construction. The jaws 30, 34 face one another opposite the tip 26 of the intermediate leg. As shown in FIGS. 1 to 3, each jaw is substantially C-shaped, when viewed from the end thereof, and the inner surface of each jaw has a radius of curvature slightly greater than that of the spherical tip 26. Each of the jaws may be coated with a plastic material to soften the clamping surfaces.

The locking mechanism 40, shown in its unengaged position in FIG. 1, includes a pin 42 mounted to the lower handle 12 and terminating in a triangular engagement tip 43 having a camming surface 44 and a bottom edge 45. A disengagement member 48 extends from upper handle 16, has a camming surface 49 for engaging against camming surface 44 of tip 43 forcing tip 43 slightly distally to release it from engagement with the opening 46 of the intermediate handle 14.

In use, depression of the button 22 causes both the upper handle 16 and the intermediate handle 14 to move together (due to their connection by shaft) in the downward direction towards lower handle 12. Sufficient downward movement causes the engagement tip 43 to extend through the opening 46 in the intermediate handle 14 until the bottom edge 45 rests on the top surface 15 of the intermediate arm 14.

Figure 5:
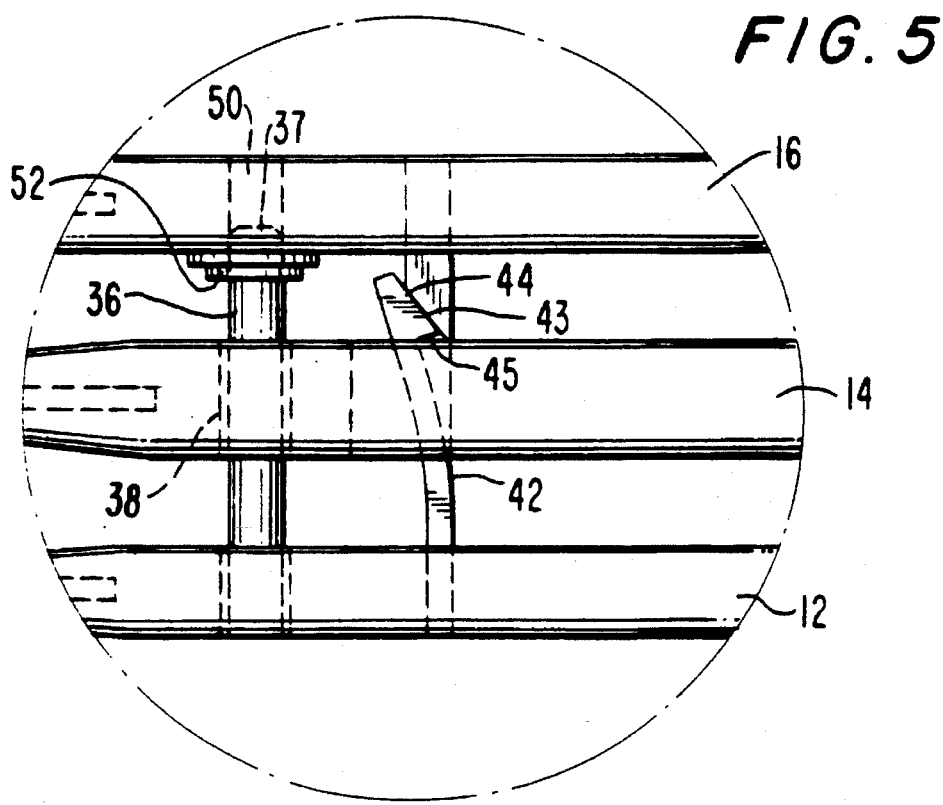
FIG. 5 shows a detailed side view of the locking mechanism of the present invention shown locked and partially unlocked.

Thus the lower handle 12 is locked relative to the intermediate handle 14 as the flange tip 44 extends through and engages the intermediate handle 14. However, the upper handle 16 is still free to move. Such movement is accomplished by once again depressing the upper handle 16 preferably in an area either proximally or distally to the button 22 towards intermediate handle 14. Since intermediate handle 14 is prevented from moving by locking mechanism 40 such depression of upper handle 16 this time moves it relative to intermediate handle 14. Referring to FIG. 5, depression of the upper handle 16 in the direction of the lower handle 12 causes the camming surface 49 of the disengagement member 48 to ride along the camming surface 44 of engagement flange 43 and force the engagement flange 43 distally and out of engagement with the intermediate handle 14.

The forceps 10 of the present invention also include a stabilizing member 36 which extends from the lower handle 12. Stabilizing member 36 extends through an opening 38 in the intermediate handle 14 when the locking mechanism is in its engaged position, i.e. when intermediate handle 14 and lower handle 12 are locked in engagement, as shown in FIGS. 2 and 5. The stabilizing member 36 further extends through an opening 50 and through guide 52 when the upper handle 16 is depressed, as best shown in FIGS. 3 and 5. Thus stabilizing member 36 lists lateral movement of the handles during use.

As is best seen in FIG. 1, the three jaws normally are maintained spaced apart from one another, with the intermediate jaw centered between the arcuate jaws, by the natural resilience of the legs, thus providing a bias against any squeezing action applied by the surgeon.

In use the spherical jaw 26 is positioned within the vessel lumen and the lower jaw 30 is positioned against the outside of a vessel. Applying pressure first between the thumb and middle finger tip, the surgeon grasps and partially everts the vessel held between lower jaw 30 and tip 26. The lower handle 12 and lower jaw 30 are locked relative to the intermediate handle 14 and tip 26, by depressing the button 22 towards the intermediate handle 14, thereby retaining the first vessel in the jaw and giving the surgeon a free finger and eliminating the necessity caused by having to maintain the first vessel engaged between the lower jaw 30 and intermediate tip 26. Then, while still grasping the first vessel, the jaw 26 is inserted into the lumen of the second vessel, with the jaw 34 on the outside of the second vessel. By applying pressure to the outer surface of the handle 16 with an index finger, the surgeon grasps the second vessel edge, similarly everting it, and holding the two edges in apposition for convenient application of a clip or other connector. Because the required manipulation is simple, a single surgeon may perform the manipulation of the everting and clipping tools in the process. Once a first suture, staple or clip has been applied, the eversion tends to remain stable, and the forceps 10 can be withdrawn while the remaining dips or sutures are applied. Note that the locking mechanism 40 is released by depressing the handle 16 causing the camming surface 49 to engage along surface 44 of flange 43 until flange 43 drops through opening 46.

While the preceding paragraphs describe an anastomosis, it should be understood that the forceps is not limited to such uses. In fact, the forceps can be used for effecting skin closures, using sutures or staples to join the approximated edges of the skin. This is particularly relevant in skin closures by staples where assistance ordinarily is necessary to maintain skin eversion, since the instrument eliminates the need for an assistant.

Other variations and modifications of the invention may occur to those of skill in the art. It is therefore intended that the foregoing be regarded as merely illustrative of the invention, which should be measured by the claims that follow.

What is claimed is:

1. An everting forceps comprising:

first and second outer resilient legs rigidly interconnected at one end thereof, each of said outer legs terminating at a tip provided with an arcuate jaw;

a third leg intermediate said outer legs and interconnected at said one end of said outer legs;

means for moving the intermediate leg with respect to one of the first and second legs;

a locking mechanism for locking said intermediate leg and at least one of said outer legs positioned on said everting forceps; and means for disengaging said locking member positioned on said everting forceps.

2. The invention of claim 1, wherein said disengaging means comprises a camming surface for contacting a camming surface on said locking mechanism.

3. The invention of claim 1, wherein said locking mechanism extends from said first leg and includes an elongated locking member movable into engagement with said intermediate leg.

4. The invention of claim 3, wherein movement of said second leg towards said first leg causes said locking member to engage said intermediate leg.

5. An everting forceps comprising:

first and second outer resilient legs rigidly interconnected at one end thereof;

a third leg intermediate said outer legs and interconnected at said one end of said outer legs;

said outer and intermediate legs having respective tips at their free ends, said tips of said outer legs being provided with cooperating jaws;

externally manipulable means positioned on said first leg for enabling one to move the intermediate leg with respect to said second leg by manually applying pressure to said first leg; and a locking mechanism positioned on said everting forceps for locking said second outer leg relative to said intermediate leg, said locking mechanism having an elongated locking member movable into engagement with said intermediate leg, said locking mechanism further having a means for disengaging said locking mechanism from engagement with said intermediate leg.

6. The invention of claim 5, wherein said disengaging means has a camming surface for contacting a camming surface on said locking mechanism.

7. A forceps for everting vessels comprising:

first and second outer legs rigidly interconnected at one end thereof and comprised of resilient material;

a third leg positioned between said first and second legs;

said first and second legs being independently movable;

means for interlocking at least one of said outer legs and said intermediate leg upon movement of said at least one outer leg, said locking means being positioned on said forceps; and means for disengaging said interlocking means to disengage said one leg and said intermediate leg, said locking means being positioned on said forceps.

8. The invention of claim 7, wherein interlocking means comprises a locking member positioned on said first outer leg, said locking member being engaged with said intermediate leg upon movement of said second outer leg and said intermediate leg.

9. The invention of claim 8, wherein said intermediate leg is attached to said second leg such that movement of said second leg towards said first leg also moves said intermediate leg towards said second leg.

10. The invention of claim 9, wherein movement of said intermediate leg toward said first leg automatically causes engagement of said interlocking means.

11. The invention of claim 8, wherein after said interlocking means is engaged, movement of said first leg towards said intermediate leg pivots said interlocking means to a disengagement position.

12. The invention of claim 11, wherein release of said first leg causes said interlocking means to disengage from said intermediate leg thereby allowing said first leg to move away from said intermediate leg.

13. The invention of claim 11, where,in said disengaging means is positioned on said second leg and includes an elongated member having a camming surface, said camming surface contacting said interlocking means to disengage said interlocking means.

14. The invention of claim 7, wherein said interlocking means comprises an elongated member extending from said first leg towards said intermediate leg said intermediate leg having an aperture to receive said elongated member.

15. Everting forceps comprising:

first and second cantilevered legs interconnected adjacent respective first ends and having second free ends spaced in juxtaposed relation and movable with respect to each other;

a third cantilevered leg connected adjacent a first end intermediate to said first and second legs and movable with respect thereto;

means for locking said third leg to one of said first and second legs in a locked position, said locking means being positioned on said everting forceps; and means for disengaging said locked legs, said disengaging means being positioned on said everting forceps.

16. The invention of claim 15 wherein said disengaging means extends from the other of said first and second legs in juxtaposed alignment with said locking mechanism and is movable in the locked position to engage said locking means to disengage said third leg and said one of said first and second legs.

17. The invention of claim 15 wherein said locking means comprises a locking member extending from said first leg and movable into engagement with said third leg.

18. The invention of claim 17 wherein said locking means comprises a locking member extending from said first leg and movable into engagement with said third leg.

19. The invention of claim 18 wherein said disengaging means extends from said second leg and is movable to engage said locking member to disengage said first and third legs.

20. The invention of claim 19 wherein said third leg comprises a throughbore through which said locking member extends, said locking member having a distal camming surface and a proximal shoulder, said camming surface facilitating entry of said locking member into said throughbore, and said shoulder engaging the side of said third leg to lock the first and third legs together.

21. The invention of claim 20 wherein said disengaging means comprises a disengaging member having a camming surface, said disengaging member camming surface being movable into camming engagement with said locking member camming surface to disengage said shoulder from the side of said third leg.

22. The invention of claim 18, further comprising means mounted on said second leg for positioning said third leg with respect to said first leg.

23. The invention of claim 15 further comprising a stabilizing member positioned on one of said first and second cantilevered legs for limiting movement of said first and second legs.

24. The invention of claim 23 wherein said stabilizing member is a rod extending from one of said first and second legs through an opening in said third leg and extending at least partially through the other one of said outer legs.

25. The invention of claim 15, wherein said first and second legs terminate at an arcuate jaw positioned and configured to cooperate with a tip of said third leg which is a spherical jaw.

26. Everting forceps comprising:

first and second cantilevered legs interconnected adjacent respective first ends having second free ends spaced in juxtaposed relation and movable with respect to each other;

a third cantilevered leg connected at a first end intermediate to said first and second legs and movable with respect thereto;

a locking mechanism connected to one of said first and second legs, said locking mechanism being movable into engagement with said third leg to lock said one leg and said third leg together in a locked position; and a disengaging mechanism positioned on the other of said first and second legs, said disengaging mechanism being movable into engagement with said locking mechanism in the locked position to disengage said one leg and said third leg.

27. The invention of claim 26 wherein said disengaging mechanism connected to the other of said first and second legs is disposed in juxtaposed alignment with said locking mechanism.

28. The invention of claim 26 wherein said locking mechanism comprises a locking member that extends from said first leg.

29. The invention of claim 28 wherein said disengaging mechanism comprises a disengaging member extending from said second leg.

30. The invention of claim 29 wherein said disengaging member extends from said second leg and is movable to engage said locking member to disengage said first and third legs.

31. The invention of claim 30 wherein said third leg comprises a throughbore through which said locking member extends, said locking member having a distal camming surface and a proximal shoulder, said camming surface facilitating entry of said locking member into said throughbore, and said shoulder engaging the side of said third leg to lock the first and third legs together.

32. The invention of claim 31 wherein said disengaging means comprises a disengaging member having a camming surface, said disengaging member camming surface being movable into camming engagement with said locking member camming surface to disengage said shoulder from the side of said third leg.

33. The invention of claim 29 further comprising a button head positioned on said second leg and having an extension slidably extending through an aperture in said second leg, the distal end of said extension being connected to said third leg, said button head being movable to position the third leg with respect to the first leg.

34. The invention of claim 26 comprising a stabilizing member positioned on one of said first and second legs to maintain alignment between said legs.

35. The invention of claim 34 wherein said stabilizing member comprises a rod extending from one of said first and second legs through an opening in said third leg and extending at least partially through the other one of said first and second legs.

* * * * *